United States Patent [19]
Aoki et al.

[11] Patent Number: 6,136,551
[45] Date of Patent: *Oct. 24, 2000

[54] ASSAY FOR DETECTING THE PRESENCE OF BOTULINUM TOXIN NEUTRALIZING ANTIBODIES IN A PATIENT SERUM SAMPLE

[75] Inventors: Kei Roger Aoki, Laguna Hills; Athena F. Spanoyannis, Tustin, both of Calif.

[73] Assignee: ALLERGAN, Inc., Irvine, Calif.

[ * ] Notice: This patent is subject to a terminal disclaimer.

[21] Appl. No.: 09/044,194

[22] Filed: Mar. 17, 1998

Related U.S. Application Data

[63] Continuation-in-part of application No. 08/426,796, Apr. 24, 1995, Pat. No. 5,731,161.

[51] Int. Cl.$^7$ .................. G01N 33/53; G01N 33/561; G01N 33/544; A61K 39/02; C12Q 1/70
[52] U.S. Cl. .................. 435/7.32; 435/7.32; 435/7.92; 435/5; 436/516; 436/528; 436/531; 436/532; 422/55; 422/56; 422/57; 424/236.1; 424/239.1; 424/247.1; 204/456; 204/462
[58] Field of Search .................. 435/7.32, 7.92, 435/5; 436/516, 528, 531, 532; 422/55–57; 424/236.1, 239.1, 247.1; 204/456, 462

[56] References Cited

U.S. PATENT DOCUMENTS 4,452,901 6/1984 Gordon et al. .................. 436/506

OTHER PUBLICATIONS

De Maio, A. protein blotting and immunoblotting using nitrocellulose membranes. in:Dunbar,B.S, Protein blotting: a practical approach (New York, Oxford University press 1994, pp. 11–14.

Siegel S, Lynn, Human immune response to botulinum pentavalent toxoid determined by a neutralization test and by an enzyme linked immunosorbent assay. Jou.Clinical microbiology, 26, (11) 2351–2356, 1988.

*Primary Examiner*—Nita Minnifield
*Assistant Examiner*—Padma Baskar
*Attorney, Agent, or Firm*—Walter A. Hackler

[57] ABSTRACT

An assay for the identification of neutralizing botulinum antibodies in sera is provided which includes the steps of separating non-sodium dodecyl sulfate, non-trypsinized complex botulinum toxin in an arylamide gel by electrophoresis, the separation occurring on a basis of botulinum toxin protein size and charge. Thereafter, the separated protein is electrophoretically transferred onto a solid support, the transferred separated protein being bound to the solid support at spaced apart sites. Remaining sites on the solid support not occupied by bound protein are blocked and the solid support and bound protein are contacted with a sera sample containing an antibody directed against botulinum toxin. The contacted solid support is then exposed to a second antibody capable of reacting to produce an insoluble colored substrate of intensity relative to a quantity of antibodies present. Finally, the second antibody is reacted to produce the insoluble colored substrate which is visually identified.

7 Claims, 1 Drawing Sheet

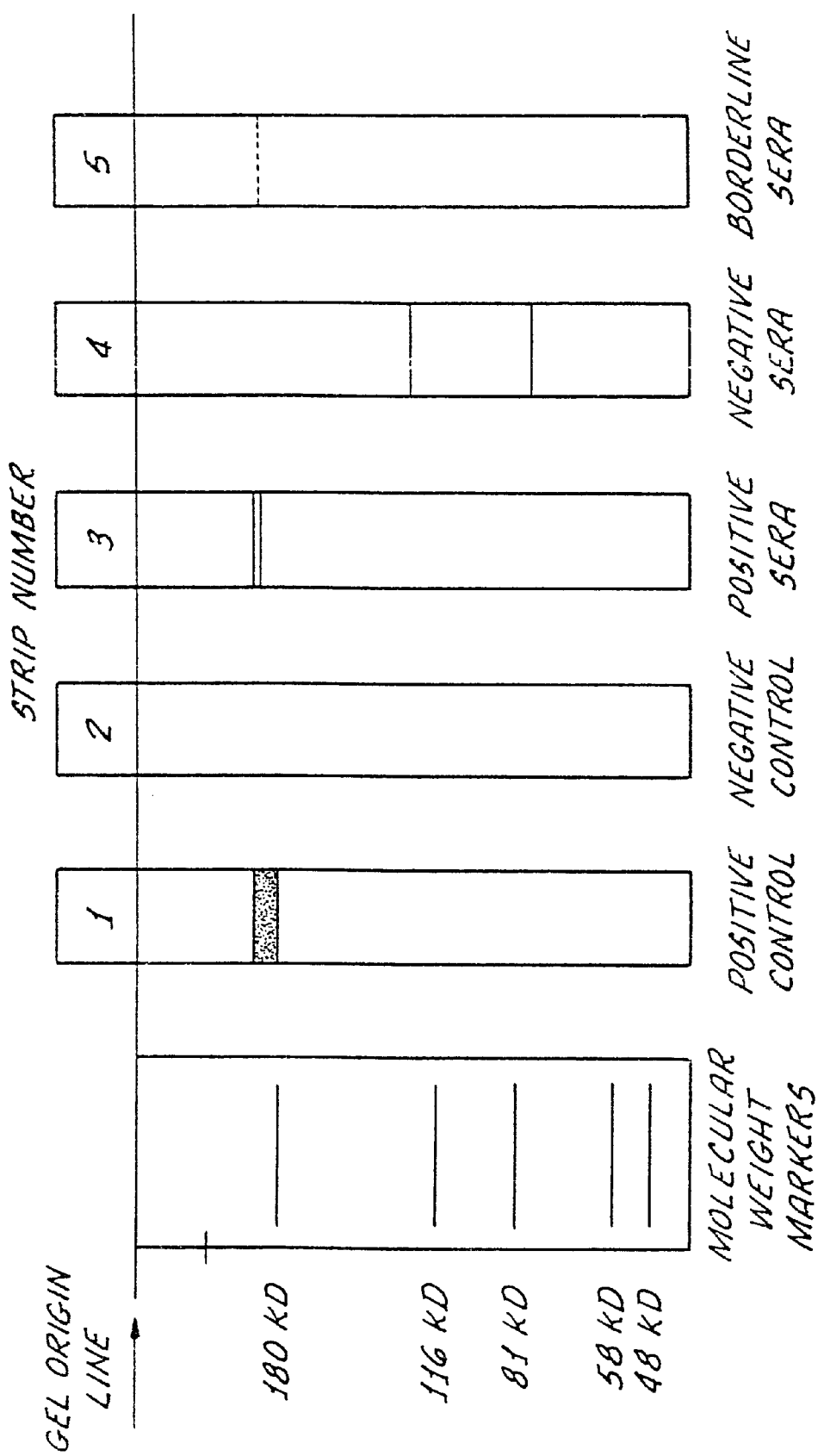

ASSAY FOR DETECTING THE PRESENCE OF BOTULINUM TOXIN NEUTRALIZING ANTIBODIES IN A PATIENT SERUM SAMPLE

This application is a continuation-in-part application of U.S. Ser. No. 08/426,796, filed Apr. 24, 1995, now U.S. Pat. No. 5,731,161.

The present invention generally relates to an improved immunoassay method and is more particularly directed to an assay for detecting antibodies to botulinum toxin in human sera by visual identification and quantitation of antibody/antigen complexes A bacterial toxin, botulinum toxin, in particular botulinum toxin type A, has been used in the treatment of a number of neuromuscular disorders and conditions involving muscular spasm; for example, strabismus, blepharospasm, spasmodic torticollis (cervical dystonia), oromandibular dystonia and spasmodic dysphonia (laryngeal dystonia). The toxin binds rapidly and strongly to presynaptic cholinergic nerve terminals and inhibits the exocytosis of acetylcholine by decreasing the frequency of acetylcholine release. This results in local paralysis and hence relaxation of the muscle afflicted by spasm.

For one example of treating neuromuscular disorders, see U.S. Pat. No. 5,053,005 to Borodic, which suggests treating curvature of the juvenile spine, i.e., scoliosis, with an acetylcholine release inhibitor, preferably botulinum toxin A.

For the treatment of strabismus with botulinum toxin type A, see Elston, J. S., et al., *British Journal of Ophthalmology*, 1985, 69, 718–724 and 891–896. For the treatment of blepharospasm with botulinum toxin type A, see Adenis, J. P., et al., *J. Fr. Ophthalmol.*, 1990, 13 (5) at pages 259–264. For treating squint, see Elston, J. S., *Eye*, 1990, 4(4):VII. For treating spasmodic and oromandibular dystonia torticollis, see Jankovic et al., *Neurology*, 1987, 37, 616–623.

Spasmodic dysphonia has been treated with botulinum toxin type A. See Blitzer et al., *Ann. Otol. Rhino. Laryngol*, 1985, 94, 591–594. Lingual dystonia was treated with botulinum toxin type A according to Brin et al., *Adv. Neurol.* (1987) 50, 599–608. Finally, Cohen et al., *Neurology* (1987) 37 (Suppl. 1), 123–4, discloses the treatment of writer's cramp with botulinum toxin type A.

The term botulinum toxin is a generic term embracing the family of toxins produced by the anaerobic bacterium *Clostridium botulinum* and, to date, seven immunologically distinct neurotoxins serotype have been identified. These have been given the designations A, B, C, D, E, F and G. For further information concerning the properties of the various botulinum toxins, reference is made to the article by Jankovic and Brin, *The New England Journal of Medicine*, Vol. 324, No. 17, 1990, pp. 1186–1194, and to the review by Charles L. Hatheway in Chapter 1 of the book entitled *Botulinum Neurotoxin and Tetanus Toxin*, L. L. Simpson, Ed., published by Academic Press Inc. of San Diego, Calif., 1989, the disclosures in which are incorporated herein by reference.

Botulinum toxin is obtained commercially by establishing and growing cultures of *C. botulinum* in a fermenter and then harvesting and purifying the fermented mixture in accordance with known techniques.

Botulinum toxin type A, the toxin type generally utilized in treating neuromuscular conditions, is currently available commercially from several sources; for example, from Porton Products Ltd. UK, under the trade name "DYSPORT," and from Allergan, Inc., Irvine, Calif., under the trade name BOTOX® Botulinum Toxin Type A purified complex.

It has been found, however, that some patients experience a loss of clinical responsiveness to botulinum toxin injections. One explanation for this action is that the patient has developed neutralizing antibodies or an immune response to a particular botulinum toxin.

Prior to the present invention, the only way to discern whether patients have antibodies to botulinus toxin was to mix the patient's serum with toxin and administer a lethal dose to mice. If the human serum showed a protective effect compared to normal human serum, then the presence of neutralizing antibodies in the patient was inferred. This mouse bioassay is slow, indirect and subject to wide variability. Further, previous inmmunoassays failed to distinguish neutralizing antibodies.

The present invention provides for the first direct method which will detect antibodies to the botulinum toxin in human sera by visual identification and quantitation of the antibody/antigen complex.

SUMMARY OF THE INVENTION

In accordance with the present invention, an assay for the identification of botulinum antibodies in sera generally includes steps of separating non-sodium dodecyl sulfate, non-trypsinized complex botulinum toxin in an acrylamide gel by electrophoresis. Because the botulinum toxin is not treated with sodium dodecyl sulfate (SDS), there is no alteration of the botulinum antigen. This is to be contrasted with electrophoretic separation as will be hereinafter discussed in greater detail.

Since SDS is not used, the separation that occurs in the gel occurs on the basis of the botulinum toxin protein size, as well as its electrical charge.

Following the electrophoresis separation, the separated protein is electrophoretically transferred onto a solid support with the transferred separated protein being bound to the solid support at spaced apart sites. All remaining sites on the solid support not occupied by the bound protein are blocked. Thereafter, the solid support and protein are contacted with a serum sample containing antibodies directed against botulinum toxin. Thereafter, the contacted solid support is exposed to a second antibody capable of reacting to produce an insoluble colored substrate of intensity relative to a quantity of antibody present.

Thereafter, the second antibody is reacted to produce the insoluble colored substrate which is visually identified.

More particularly, the method of the present invention may utilize a solid support comprising nitrocellulose which may be dried after the electrophoretic transfer and before blocking in order to improve protein binding. The step of blocking all remaining sites may comprise soaking the solid support in a blocking agent which may be, for example, nonfat dried milk, or any protein such as albumin.

Still, more particularly, the acrylamide concentration in the acrylamide gel is about 7.5%. The electrophoretic movement of the complex botulinum toxin in the gel may be monitored by applying prestained molecular weight markers in the acrylamide gel. The second antibody may be labeled with alkaline phosphatase and the step of reacting the second antibody may comprise oxidizing the second antibody labeled the alkaline phosphates with a substrate producing a collered precipitate.

BRIEF DESCRIPTION OF THE DRAWING

The advantages and features of the present invention may appear from the following description when considered in conjunction with the accompanying FIG. 1 which is a representation of antigen/antibody bands appearing on solid substrates as will hereinafter be described in greater detail.

DETAILED DESCRIPTION

Proteins may be separated with a high degree of resolution on the basis of their molecular weight using SDS-polyacrylamide gels.

SDS is a negatively charged, denaturing detergent that binds to a protein in proportion to that protein's mass. The negative charge of the bound SDS is thought to unfold the protein and force it into the conformation of an extended, flexible rod. This conformational change is ensured if all of the intramolecular and intermolecular disulfide bonds are broken by simultaneously treating the protein with SDS and a reducing agent (e.g., DTT or β-mercaptoethanol). The sizes of these flexible rods vary with the molecular weight of the protein, but all proteins have a similar charge density (charge per unit of mass) because the negative charge of the bound detergent almost completely masks the intrinsic charge of the protein.

When an electric field is applied to SDS-denatured proteins in solution, all of the proteins move at the same speed, regardless of size, because they all have a similar charge density and the same friction per unit of rod length. The total charge in the larger proteins (longer rods) is greater and therefore more force is generated for forward movement, but the total friction opposing forward movement is also greater, making these proteins move at the same speed as the smaller ones.

When an electric field is applied to SDS-denatured proteins in an SDS-polyacrylamide gel matrix, the proteins move at different rates. The longer the flexible protein rod, the more frequently the rod becomes entwined in the gel matrix and the slower it moves through the gel. Thus, the smaller proteins move a greater distance than the longer rods in the same period of time. The result is that the gel matrix acts as a sieve and separates the SDS-denatured proteins according to their masses. A straight line results from plotting the logarithms of the molecular weights of most proteins versus the distances they migrate through an SDS-polyacrylamide gel, but not all proteins display this ideal behavior during electrophoresis. A protein's electrophoretic mobility can be altered if, for example, it has either a large number of positive charges or several-carbohydrate chains. A large number of positive charges decreases the negative charge density imposed by the bound SDS. The carbohydrate chains may change the amount of SDS bound per unit of mass and therefore change the charge density.

When proteins are separted by electrophoresis in the absence of SDS, they are separted by charge, shape and molecular weight. This method is commonly referred to as a native gel.

It has been found that the SDS treatment of protein, which is now considered standard, for providing definitive movement of the protein through acrylamide gels is, in fact, deleterious to botulinum toxin when utilized in an electrophoresis-based assay. That is, consistent antibody binding results cannot be obtained. Similar effects occur when a botulinum toxin is trypsinized. Consequently, according to conventional thought, complex botulinum toxin, which has not been trypsinized or treated with SDS, can be utilized in an assay for antibodies, particularly when using native gel western blot techniques.

The typical western blot method is described in U.S. Pat. No. 4,452,901, which describes the procedures necessary to transfer antigenetic tryptides from a single gel to nitrocellulose. This reference is incorporated herein in toto for the purpose of explaining and defining the western blot method.

In general, however, western blotting, also known as immunoblotting, is used to identify specific antigens recognized by polyclonal or monoclonal antibodies.

Protein samples are solubilized, usually with sodium dodecyl sulfate (SDS) and reducing agents such as dithiothreitol (DTT) or 2-mercaptoethanol (2-ME). Following solubilization, the material is separated by SDS and the antigens are then electrophoretically transferred in a tank (first basic protocol) for a semidry unit (first alternate protocol) to a nitrocellulose, PVDF, or nylon membrane, a process that can be monitored by a reversible staining procedure (support protocol).

The transferred proteins are bound to the surface of the membrane, providing access for reaction with immunodetection reagents. All remaining binding sites are blocked by immersing the membrane in a solution containing either a protein or detergent blocking agent. After probing with the primary antibody, the membrane is washed and the antibody-antigen complexes are identified with horseradish peroxidase (HRPO) or alkaline phosphatase enzymes coupled to the secondary anti-lgG antibody (e.g., goat anti-rabbit IgG). The enzymes are attached directly (second basic protocol) or via an avidin-biotin bridge (second alternate protocol) to the secondary antibody. Chromogenic or luminescent substrates (third basic and alternate protocols) are then used to visualize the activity.

Immobilized proteins are probed with specific antibodies to identify and quantitate any antigens present. The membrane is immersed in blocking buffer to fill all protein-binding sites with a nonreactive protein or detergent. Next, it is placed in a solution containing the antibody directed against the antigen (primary antibody). The blot is washed and exposed to an enzyme-antibody conjugate directed against the primary antibody (secondary antibody; e.g., goat anti-rabbit IgG). Antigens are identified by chromogenic or luminescent visualization (third basic and alternate protocols) of the antigen/primary antibody/secondary antibody/enzyme complex bound to the membrane. TWEEN-20 (TBS-T-20) is a popular alternative to protein-blocking agents when using nitrocellulose or PVDF filters.

In general, the method of the present invention may be described as follows:

The large molecular weight (500–900 kD) complex of Botulinum Neurotoxin Type A (BoNT/A) received in a solution of 0.2M sodium chloride, 0.05M sodium acetate, pH 6.0, is reduced by the addition of 0.1M final concentration of dithiothreitol (DTT). 22.5 μg of reduced toxin is then combined with an equal volume of 2× Native Gel Sample Buffer and immediately loaded onto a precast 8% acrylamide (8%T/2.6%C) Tris-glycine Native-PAGE minigel (NOVEX). This minigel is 1.0 mm in thickness and contains one "trough" well and one reference well. The trough well spans approximately eight lanes of a ten-lane, *×10 minigel. The 2× Native Gel Sample Buffer consists of 1.5M Tris-HCl, pH 8.8, 20% glycerol and 0.1% Bromophenol blue. The Native gel running buffer is 0.024M Tris-base, 0.192M Glycine, approximate pH 8.3.

The gel is electrophoresed at 100 volts (constant voltage) until the Bromophenol blue dye-front electrophoreses out of the bottom of the gel. Upon completion, the gel sandwich is opened, the gel removed and placed directly against a sheet of 0.45 μm pore size nitrocellulose membrane (Schleicher & Schuel #BA85). The proteins are then electrophoretically transferred to the nitrocellulose at 200 mAmps (constant current) for a total of 2 hours run time. After transfer, the membrane (or blot) is allowed to air dry prior to immunoblotting procedure. The transfer buffer consists of 0.133M Glycine, 0.02M Tris-base, 15% Methanol.

For immunoblotting, the membrane is sandwiched into an incubation chamber which creates 10 separate, vertical, liquid-tight chambers against the entire length of the blot (Mini-Decaprobe Unit by Hoefer Sci.). This device allows 10 individual patient serums to be analyzed on the membrane without having to slice the membrane into individual strips.

Unbound protein-binding sites on the blot are blocked with a solution of 5% nonfat dried milk in 0.15M sodium chloride, 0.01M Tris, pH 8.0, 0.05% (v/v) TWEEN-20 (TBS-T-20). The blot is incubated in this solution for two hours at room temperature with gentle agitation on a rocking platform. The blocking solution is then gently aspirated out of the unit and ten clinical patient human serums to be tested are applied into designated chambers. These human serums are initially tested against the blot at a dilution of 1:300 using 2% nonfat dried milk in TBS-T-20 as the diluent. The sera samples are allowed to incubate for two hours at room temperature with gentle agitation on a rocking platform. After the primary incubation, the sera samples are gently aspirated out of the chambers.

Each chamber is then washed with a solution of TBS-T-20 for ten minutes per wash with a total of three washes. The washes are performed at room temperature with medium agitation on a rocking platform.

The blot is then incubated with a secondary anti-body-enzyme conjugate which recognizes human IgG and possesses alkaline phosphatase to allow chromogenic visualization. The antibody is Goat anti-human IgG-alkaline phosphatase conjugate (Promega) used at a 1:7,000 dilution in 2% nonfat dried milk in TBS-T-20. This secondary antibody is incubated on the blot for one hour at room temperature with gentle agitation on a rocking platform.

Each chamber is then washed with a solution of TBS-T-20 for ten minutes per wash with a total of three washes. The washes are performed at room temperature with medium agitation on a rocking platform.

The blot is then removed from the incubation chamber, rinsed briefly in TBS (no TBS-T-20) and then immersed in a container of color development substrate for the alkaline phosphatase activity. Incubation in the NBT/BCIP Color Development Solution (Promega) results in a blue-purple color deposit on the membrane at the site of antigenic specificity of the human clinical sera.

Resulting color deposits on the blot enable comparisons of immunopatterns between volunteers immunized against BoNT/A-E, patients receiving BOTOX® treatments and normal, untreated volunteers.

The present assay results in a positive pattern of at least two or more bands for immunized volunteers and patients termed "secondary non-responders"; however, normal volunteers and patients termed "responders" usually do not demonstrate any banding pattern. This assay can provide a yes/no determination for the presence of neutralizing antibodies to botulinum toxin.

It should also be appreciated that the present invention, utilizing non-SDS, non-trypsinized complex botulinum toxin may be practiced in "dot blotting". that is, an antigen in solution can be detected by simply spotting the solution on nitrocellulose and then "staining" it with primary and secondary antibodies (as in western blotting) to produce a dot blot. Dot blots can be used in lieu of the western blot assay or it can be used to determine quickly how much of an extract to use for a western blot or used to determine whether or not the epitope of interest will survive the western blotting procedure.

Although dot blots provide a fast and simple method for measuring antigen concentrations, they have some limitations. One of the most important is that antigens present in low concentrations in crude extracts can be prevented from binding to the nitrocellulose by other proteins present in high concentrations. Because the antigens must compete for the limited surface on which to bind, the antigens present in high concentrations can more rapidly saturate the surface.

Dot blotting may be performed in a number of methods. For example, a Hamilton syringe or-variable pipette may be used to spot very small aliquots (1–2 $\mu$l) of a protein sample on dry nitrocellulose. Alternatively, a suction manifold may be used to apply large volumes (10–1,000 $\mu$l). In both methods, the spotted samples are exposed to primary and secondary antibodies, as hereinabove described. The method using the syringe or pipette works well if only 1–10 $\mu$l of antigen solution is needed to obtain a good signal. Applying large volumes of samples to nitrocellulose by this method can be tedious; several rounds of application and drying are required to keep the antigen concentrated in a small spot. large volumes of samples are more easily applied to nitrocellulose using a suction manifold, which uses a vacuum to pull the samples through nitrocellulose mounted in a plastic holder that contains holes through which the samples are applied.

DETAILED PROCEDURE DESCRIPTION (a) Chemicals and Reagents

NOTE: All chemicals were obtained from Sigma Chemical Co. (P.O. Box 14508, St. Louis, Mo. 63178, USA) or from BioRad Corp. (P.O. Box 708, 220 Maple Avenue, Rockville Center, New York, N.Y. 11571 USA) or equivalent. All chemicals were reagent grade unless otherwise specified.

Acrylamide (BioRad Order No. 47033A),
Ammonium persulfate (Sigma Order No. A-6761)
Anti-Human IgG (H+L) alkaline phosphatase conjugated antibody (Promega Corp. Order No. S3821)
Bis-acrylamide (BioRad Order No. 47803A)
Botox Complex (BoNT/A) antigen (Non-SDS, undigested) 0.9 $\mu$l/$\mu$l (Allergan)
5-Bromo-4-Chloro-3-Indoyl Phosphate (BCIP) (Sigma Order No. B-8503)
Deionized water
Dimethyl formamide (Sigma Order No. 4254)
Glycerol (Sigma Order No. G-9012)
Glycine (Sigma Order No. G-7126)
Magnesium chloride (Sigma Order No. M-9272)
Methanol (98.9%) (VWR Order No. JT9093-02)
N-Butanol (99%) (Sigma Order No. BT-105)
Nitroblue tetrazolium (Sigma Order No. N-6876)
N,N,N',N'-tetramethylethylenediamine (TEMED) (Sigma Order No. T-8133)
Nonfat dry milk (Carnation Foods Inc., Los Angeles, Calif.)
Prestained SDS-molecular weight markers (MW 26.6, 36.5, 48.5, 58.0, 84.0, 116.0, 180.0 kd, MW-SDS-Blue, Sigma Chemical Corp.)
RBS-35 (cleaning solvent) (Pierce Chemical Co. Order No. 27952)

Sodium chloride (NaCl) (J. T. Baker Inc.)
Sodium hydroxide (NaOH) (122.5N) (VWR Order No. VW6730-7)
Tris-base (Sigma Order No. T-1503)
Tris-Glycine Native Running buffer 10× (Novex Order No. LC2672)
Tris-Glycine Native Sample buffer 2× (Noves Order No. LC2673)
TWEEN 20 (Sigma Order No. P-1379)

(b) Solutions

Solution 1: 1M Tris-base Stock (pH 6.8)
Add 60.55 gm Tris-base to 350 ml water, adjust pH to 6.8 using 12 N concentrated HCl. Adjust volume to 500 ml with deionized water.

Solution 2: Acrylamide Stock Solution (30%)
Add 150 gm acrylamide to 350 ml water, mix gently until dissolved. Add deionized water and bring to a final volume of 500 ml.

Solution 3: Bis-acrylamide (1%)
Add 1 gm bis-acrylamide to 99 ml water, mix gently until dissolved, add deionized water to a final volume of 100 ml.

Solution 4: 3M Tris-base, pH 8.8 Stock
Add 363 gm Tris-base to 800 ml deionized water, adjust pH, using 12N HCl to pH 8.8. Bring to a final volume of 1000 ml with deionized water. Note: Tris-base will not go into solution until HCl is added.

Solution 5: 20% Ammonium Persulfate
Add 0.2 gm Ammonium persulfate to 1.0 ml deionized water.

Solution 6: Electrophoresis running buffer (tris/glycine pH 8.5
Dilute 25 ml Novex 10× concentrated electrophoresis buffer to 250 ml final volume with deionized water.

Solution 7: Native Antigen Sample Buffer 2× (tris/glycerol Novex)
Pre-made 2× sample buffer is complete and ready to use from the bottle.

Solution 8: N-butanol saturated in water 1:1 (v/v)
Add 25 ml of water to an equal volume of n-butanol and mix. Allow the n-butanol layer to separate from the water. The top layer is the saturated n-butanol.

Solution 9: Transfer buffer-tris (0.025M); glycine (0.192m) (ICN Order No. 816200)
Empty the contents of one pre-mixed electrophoresis buffer packet into a beaker, add 3L deionized water, 800 ml methanol, and bring to a final volume of 4 L with deionized water.

Solution 10: TBST buffer (10 mM Tris-base, pH 8.0. 150 mM NaCl, 0.05% Tween 20)
Add 40 ml of 1M Tris-base (pH 8.0) (Solution No. 17), add to 36.0 gm NaCl and 2.0 ml Tween 20, bring to a volume of 4.0 L with deionized water.

Solution 11: Blocking Agent (Carnation Foods Inc. Los Angeles, Calif.) 5% (w/v) nonfat dry milk in TBST
Add 5 gm nonfat dry milk to 75 ml TBST (Solution No. 10), adjust final volume to 100 ml.

Solution 12: Dilution Buffer 2% (w/v) nonfat dry milk in TBST
Add 2 gm nonfat dry milk to 75 ml TBST (Solution No. 10), adjust final volume to 100 ml.

Solution 13: Alkaline Phosphatase Buffer (100 mM Tris-base, pH 9.5. 100 mM NaCl, and 5 mM $MfCl_2$)
Add 50 ml Tris-base 1M pH 9.5 (Solution No. 20), 20 ml NaCl 2.5M (Solution No. 18), and 2.5 ml $MgCl_2$. $6H_2O$ 1.0M (Solution No. 19), bring to 400 ml with deionized water, adjust pH to 9.5 with 12N HCl and adjust final volume to 500 ml with deionized water.

Solution 14: BCIP in DMF 10 mg/ml
Add 10 mg dimethylformamide to 100 mg BCIP.

Solution 15: NBT in Tris-base (100 mM) 2 mg/ml
Add 10 mg NBT, 0.5 ml Tris-base (1M) pH 9.5 (Solution No. 20) and 4.5 ml water to a 15 ml conical tube.

Solution 16: Color development solution
Add 45 ml Alkaline Phosphatase Buffer (Solution No. 13)., 0.5 ml BCIP/DMF (Solution No. 14) and 5.0 ml NBT/Tris-base (Solution No. 15) to a 50 ml conical tube.

Solution 17: Tris-base (1M) pH 8.0 Buffer
Add 121. gm Tris-base to 900 ml deionized water in graduated cylinder. Adjust pH to 8.0 using concentrated HCl and bring final volume to 1,000 ml with deionized water.

Solution 18: NaCl (2.5M)
Add 146.1 gm NaCl to a graduated cylinder; add deionized water and bring to a level of 1,000 ml.

Solution 19: $MgCl_2$. $6H_2O$ (1M)
Add 95.22 gm $MgCl_2$. $6H_2O$ to graduated cylinder, add deionized water and bring to a level of 1,000 ml.

Solution 20: Tris-base (1.0M) pH 9.5 Buffer
Add 121.1 gm Tris-base to 900 ml deionized water in graduated cylinder. Adjust pH to 9.5 using concentrated HCl and bring final volume to 1,000 ml with deionized water.

(c) Equipment

| | |
|---|---|
| Brinkman Instruments, Inc. Westbury, NY 11590 | 0–100 µl; 100–1,000 µl Eppendorf Micropipetts |
| Mettler Inst. Corp., Hightstown, NJ 08520 | Mettler balance-Model AE240 Mettler balance-Model PJ6000 |
| Beckman Instruments Inc. Palo Alto, CA 94304 | Beckman centrifuge Model TJ-6 |
| Hoefer Scientific San Francisco, CA | Red Rocker-orbital rocking platform Mighty Small II Electrophoresis Unit SE-250 Electrophoresis power supply Mighty Small Transphor System, TE 22 Blotter Paper, TE 26 |
| Schleicher and Suhuell Keene, NH | Nitrocellulose paper 0.45 micron pore size No. 21640 Incubation Trays No. 40560 |

(d) Assay Control Samples (1) Positive Control (i) Source: The positive control samples were serum from individuals immunized with botulinum toxoid (A-E) confirmed positive by the mouse bioassay and validated a minimum of three times in the Western blot assay. The sera were performed at 3 dilutions to establish assay sensitivity. The first dilution was equivalent to the standard dilution for all samples, 1:300. The second dilution, 1:3,000, confirmed the medium-end sensitivity of the current assay. The 3rd dilution, 1:10, 000, confirmed the high-end sensitivity of the current assay.

(ii) Directions for Preparation: An aliquot of the positive control serum sample was stored at −20° C. and allowed to thaw at room temperature. Positive serum was diluted 1:300, 1:3,000 and 1:10,000 in diluting buffer (Solution No. 12).

(2) Negative Control (i) The negative control sample was serum from a healthy individual without prior exposure to botulinum toxin. The sample was prepared and stored in assay-sized aliquots at −20° C. this control was validated as negative by the Wester blot assay. This sample was run at the dilution 1:300.

(ii) Directions for Preparation: An aliquot of the negative control serum sample was stored at −20° C. and allowed to thaw at room temperature. Sera were diluted 1:300 in diluting buffer (Solution No. 12).

(e) Molecular Weight Markers

Reconstitute molecular weight markers according to manufacturer's specifications. Reconstituted molecular weight markers were stored in 30 μl aliquots at −80° C. Molecular weight markers were loaded at 3 μl/lane in a designated lane.

(f) Method for Electrophoresis and Transfer of Gels (1) Casting Apparatus Setup

STEP 1: Clean all spacers, aluminum plates and glass plates thoroughly with a 2% solution of RBS-35 detergent (wearing nonpowdered gloves and using hot tap water). Rinse in deionized water. Clean the gel casting unit with hot water and rinse in deionized water. Ensure spacers, plates and casting unit are dry, using lint-free tissue.

STEP 2: Assemble 10 gel "sandwiches" in the multi-gel casting apparatus, using 20, 1.0 mm spacers, 10 aluminum and 10 glass plates.

Assemble as follows:

Place the large filler plug (triangular rubber wedge) in the base of the casting unit, trough facing upwards. Place the two small filler plugs (rubber wedges) with the flat side upwards, in the side slots of the casting unit.

Place a wax paper sheet at the back of the casting unit. Place the space saver acrylic plate against the wax sheet at the back of the casting unit; then add a second sheet of wax paper in front.

Construct a stack of 10 gel sandwiches inside the open casting chamber. Place the aluminum plate in the back of the casting unit against the wax paper with the notch upward. Place spacers along each side of the aluminum plate with the notches outward. The notches on the spine of each spacer should be flush with the outside edges of the plates. Fit a glass plate onto the spacers securing each side within the tabs of the spacers.

Place one sheet of wax paper between each sandwich to facilitate separation after polymerization. Check plate and spacer alignment for each sandwich after they have been assembled. This assembly constitutes one gel sandwich. Continue the assembly until 10 sandwiches are completed.

Place additional glass plates or polycorbinate sheets in the back of the caster to fill excess space.

Place a small amount of silicone on the front U gasket and place the front panel on the casting chamber. Clamp the front panel against the U gasket using the red clamps provided. Fit the clamps into the grooves of the front plate and casting unit, securing the front plate. Gel sandwiches must fit tightly into the casting stand.

Stand the casting unit upright and check for alignment of spacers using the provided "Spacer Mate" wedge.

Seal the red inlet port near the bottom of the front panel with the provided plug.

(2) Casting of 7.5% Acrylamide Resolving Gels

STEP 3: Obtain the following solutions:

Acrylamide Stock Solution (30%) (Solution No. 2)
Bis-acrylamide (1%) (Solution No. 3)
3.0M Tris-base, pH 8.8 Stock (Solution No. 4)
Ammonium Persulfate (20%) (Solution No. 5)
Running Buffer (Solution No. 8)

NOTE: Each gel contains approximately 6.0 ml resolving gel. Ten gels require 60 ml of acrylamide solution for the gels and the "dead space" in the multi-casting unit.

STEP 4: Use a dedicated 125 ml side-arm flask for acrylamide formulation. Be certain glass ware is detergent free by washing with water only. Detergent can cause premature polymerization. In a clean 125 ml side-arm flask, add the following:

18.5 ml 30% Acrylamide (Solution No. 2)
10.0 ml 1% Bis-Acrylamide (Solution No. 3)
9.38 ml 3M Tris (pH 8.8) (Solution No. 4)
36.25 ml Deionized water STEP 5: Seal the top of the side-arm flask and degas the gel solution under vacuum.

STEP 6: Add 125 μl of APS (Solution No. 5) and 35 μl TEMED to the degassed solution, mix well. Add 60 ml of the acrylamide solution to the first assembled gel sandwich, 10 ml at a time with a 10 ml pipette.

STEP 7: When completed, acrylamide in the first glass plate will reach a level 5.3 mm from the base of the gel. Observe the level for a few seconds to ensure all the casting plates are up to volume. Continue adding gel solution if necessary.

STEP 8: Gently overlay each resolving gel with approximately 100 μl of water saturated n-butanol (Solution No. 8). Cover the unit with plastic wrap.

STEP 9: Allow a minimum of 2 hours for gel polymerization. Keep gels out of direct sunlight.

STEP 10: Disassemble the casting unit by removing the clamps and the face plate. Take the gel sandwiches out one at a time, remove the wax paper and any residual acrylamide by rinsing with deionized water. Wrap the gels in pairs with plastic wrap. The gels may be stored for 2 weeks at 0° C.

(3) Preparation of Stacking Gel

NOTE: Stacking gels are prepared the day of gel electrophoresis.

STEP 11: Obtain the required number of gels for the daily run. Rinse the gels with deionized water and remove any excess acrylamide from the surface of the gel sandwiches. Clamp each gel sandwich to the running unit with the red clamps provided. Be sure there is sufficient space under the gel sandwiches for buffer migration.

STEP 12: Insert a 1.0 mm comb containing one large antigen well (6.7 cm) and one small well for the molecular weight markers (0.5 cm).

STEP 13: In a 125 ml side-arm flask add the following:

3.0 ml, 30% acrylamide stock (Solution No. 2)
3.5 ml 1% bis-acrylamide stock (Solution No. 3)
3.75 ml 1M Tris pH 6.8 (Solution No. 1)
19.5 ml deionized water STEP 14: Seal the top of the side-arm flask and degas the gel solution under vacuum. Add 150 μl of APS (Solution No. 5) and 60 μl TEMED to the solution; mix well.

STEP 15: Using a Pasteur pipet, apply stacking gel onto the resolving gel until the level reaches the bottom of the comb. Allow the stacking gel to polymerize for 15–30 minutes at room temperature. Keep excess tacking mixture and visually confirm polymerization. After the stacking gel has polymerized, gently remove combs as gels are needed.

(g) Antigen Preparation and Application

STEP 16: Prepare the botulinum antigen by adding antigen sample buffer 1:1 (v/v) (Solution No. 7) to the antigen. The volume for each gel is 50 μl of antigen including buffer. Example: 100 μl of antigen+100 μl of loading buffer will equal the required volume of antigen for four gels, 50 μl/gel. The concentration of each gel will be approximately 22 μg/gel.

STEP 17: Prepare 250 ml of running buffer (Solution No. 6), Fill upper electrophoresis chambers to capacity, then pour the remaining buffer into the lower chamber. Load 50 μl of the diluted antigen through the buffer into the large well. Load 3 μl of molecular weight markers into the smaller well created by the comb.

(h) Assembly of Electrophoresis Apparatus and Electrophoresis

STEP 18: Place the lid assembly onto the gel running unit with the red (+) receptacle of the lid into the red (+) prong of the running unit, and the black (−) receptacle over the black (−) prong.

STEP 19: Insert the red (+) power supply plug into the red (+) outlet of the power supply. Do the same for the black plug and the black outlet.

STEP 20: Attach the water cooling input and output supply hoses to the EP apparatus. Begin circulation of cold water through the unit. Turn on power supply and adjust output to 125 volts constant. Periodically check chamber to ensure the unit is cooling properly. Electrophoresis will require 1.5 to 2 hours.

(i) Electrophoretic Transfer to Nitrocellulose

STEP 21: Cut one piece of nitrocellulose for each gel run. A glass plate is used as the template. label the nitrocellulose in the upper left hand corner with the date and gel number and the assay name (Botox).

STEP 22: Prepare Transfer Buffer (Solution No. 9). About 1.5 liters will be needed for the Mini-Transphor unit and the transfer support unit. Pre-wet the nitrocellulose by adding transfer buffer to a tray. Lower the labeled nitrocellulose into the buffer from the bottom edge upward. The nitrocellulose should soak for a minimum of 15 minutes.

STEP 23: Prepare the electrophoretic transfer system described in U.S. Pat. No. 4,452,901.

STEP 24: Completely soak sponges, filter papers and pre-cut nitrocellulose sheets in Transfer Buffer (Solution No. 9).

STEP 25: Check the gel front, indicated by the bromophenol blue tracking dye. Electrophoresis is concluded when the dye front has reached the bottom of the gel.

STEP 26: Shut off power supply and disconnect all electrical lines to the EP apparatus. Remove the gel plates one at a time and proceed with the transfer.

STEP 27: Set gel plates horizontally on a clean bench space with the glass side sup and the aluminum side down. Carefully remove spacers from gel set-up and remove top piece of glass plate. Slice off stacking gel and discard.

STEP 28: The gel should be stuck to bottom aluminum plate. Continue with gel transfer as follows: Place one piece of dry filter paper over the gel and smooth the filter paper. Carefully lift one corner of the filter paper sheet. The gel should stick to the filter paper and lift off aluminum plate.

STEP 29: Place a transfer cassette in a buffer tray, white support side down, fill with transfer buffer (Solution No. 9) till the volume just covers the sponge supports. Place the gel/filter paper assembly on the sponge backed by the white support (negative).

STEP 30: Place pre-wetted nitrocellulose evenly on the gel, smoothing out bubbles gently with a spacer. Place a wetted piece of filter paper on top of the nitrocellulose and smooth out gently with a spacer to remove bubbles. Place a second support sponge on top of the filter paper. Close the support cassette by clipping the two halves together. Place cassette into the mini-Transphor Apparatus with positive support (black) near positive lead (red) of power supply.

STEP 31: Ensure that the transfer tank electrical leads are completely disconnected, and the power source is OFF. Fill transfer tank with Transfer Buffer (Solution No. 9), ensuring that the polarity of the gel to nitrocellulose is correct and buffer completely covers the transfer cassettes. place magnetic stir bar in the bottom of the tank.

STEP 32: Place transfer system on magnetic stirrer and turn on magnetic stirrer at speed 5–6, at room temperature. Plug the cables into the power supply so that the positive (red) cable is in the positive (red) outlet, and the negative (black) cable is in the negative (black) outlet of the power supply.

STEP 33: Insert a hose from the faucet and leading to the inlet port and a hose from the outlet port of the transfer unit to a drain; turn on the water supply.

STEP 34: Turn the power on and set output to constant current, 200 milliamps for 2 hours or 23 milliamps for overnight transfer. The proteins will transfer out of the gel and onto the nitrocellulose.

STEP 35: When the transfer interval is completed, turn off the power supply; remove the top of the transfer unit. Remove the transfer cassettes one at a time. Open the cassettes and remove the nitrocellulose. Discard the acrylamide gel and blotting papers. Let the blots dry for a minimum of 1 hour on clean blotting paper. At this step the blots can be stored for 2 weeks at room temperature before proceeding with the blocking step.

STEP 36: Prepare 100 ml of 5% milk in TBST (Solution No. 10). Gently place the nitrocellulose blots into the blocking solution. Gently rock for 1 hour at room temperature. Prior to use, rinse the blots in TBST (Solution No. 12). Retain the blots in TBST until nitrocellulose strip preparation.

(j) Nitrocellulose Strip Setup

STEP 37: Place the blot on a glass plate. Draw a line across the top of the nitrocellulose that coincides with the top edge of the gel. Put plastic wrap over the nitrocellulose.

STEP 38: Use the sample comb as a guide to determine the boundaries of the antigen lane at both sides of the gel. Cut the far right side of the blot at the start of the antigen lane and discard. Cut off excess nitrocellulose, below the bottom of the gel and discard.

STEP 39: Cut strips vertically from the top to the bottom of the blot beginning at the right side of the blot. Discard the first two strips. Cut the required number of strips necessary for the number of assay samples or continue cutting strips until the end of the antigen lane is reached. The end is approximately 5 mm to the right of the molecular weight markers. To ensure proper width, no more than 25 strips are cut from a single blot. Place any remaining blot on a dry piece of blotting paper and store in a cool dark location.

STEP 40: Label the strips by number. The positive controls are the first and second strips; the negative control, the third. Patient samples are tested using consecutive following strips. Place the strips in the incubation trays with 1 ml of TBST (Solution No. 10).

(k) Sample Dilution and Application

STEP 41: Locate and organize the controls and patient samples for the assay. Construct a worksheet (Botox Strip Worksheet), which documents the sera sample and its strip.

STEP 42: Dilute controls and patient sera sample 1:300 with 2% milk in TBST (Solution No. 12). Add 3.3 µl of serum to 1 ml of 2% milk in TBST.

STEP 43: Aspirate TBST buffer out of the chambers of the incubation tray containing the designated antigen tray and place 1 ml of diluted sample into the assigned chamber with the nitrocellulose strip. Once all samples and controls are loaded, place the incubation tray on a rocking platform. Incubate nitrocellulose with samples at room temperature at speed 3 for 2 hours.

STEP 44: After sera incubation is completed, aspirate TBST buffer out of all the chambers. Wash each strip by adding 1 ml of TBST buffer (Solution No. 10) to each chamber. Allow strips to wash for 10 minutes at room temperature on the rocking platform. Repeat the aspiration and wash 2 additional times.

STEP 45: Prepare the goat anti-human IgG second antibody by diluting it 1:7000 with 2% milk in TBST buffer (Solution No. 12). 4 µl second antibody is added to 28 ml diluting buffer.

STEP 46: Immediately following the third aspiration of the washing buffer, add 1 ml of diluted second antibody. Allow the nitrocellulose strips to incubate for 1 hour, room temperature, rocking at speed 3.

STEP 47: After incubation aspirate the second antibody from the chambers and wash each with the addition of 1 ml TBST buffer (Solution No. 10). continue rocking for 10 minutes at room temperature. Perform 2 additional washes with TBST (Solution No. 10).

(l) Immunodetection of Botulinum Toxin Antibodies on Nitrocellulose

STEP 48: Prepare color development solution (Solution No. 16). Immediately before use, obtain the following solutions:

Alkaline Phosphatase buffer (Solution No. 13)

BCIP in DEMF 10 mg/ml (Solution No. 14)

NBT in Tris-base 2 mg/ml (Solution No. 15)

STEP 49: Remove the final wash TBST buffer from the nitrocellulose strip and add 1 ml of color development solution (Solution No. 16). Rock the strips at speed 3 on the rocker platform, room temperature, for 15 minutes. Observe the high and low positive controls. A clear signal should be visible in the high positive, and a faint signal in the low positive. Stop the reaction by rapidly rinsing the strips several times with deionized water. Air dry the strips in an area free of direct light for at least 1 hour.

STEP 50: Organize the nitrocellulose strips on the "Strip Identification Worksheet". Each strip is lined up in association with its numerical order and gel origin line drawn prior to strip formation. The work sheet contains all the assay identification and patient information to insure sample/blot correlation.

(m) Western Blot Interpretation for Botulinum Specific Bands

Organization of the "Strip Identification Worksheet" allows direct comparison of positive and negative controls to the patient sera strips. Molecular weight markers corresponding to the blot from which the strips were cut is also aligned with the strips for comparative purposes.

The identification of botulinum antibodies by the Western blot assay is dependent on the presence of "reactive" patterns or a specific band. The specific band which identifies a positive response for botulinum antibodies is located at a molecular weight equivalence of 180 kD. This is the only band required for a positive result. No other bands at any location constitute a positive result.

Sera diluted at 1:300 fall into one of three categories:

(1) Negative; no bands are observed at the 180 kD range. The result is reported.

(2) Borderline; banding profile is extremely weak or indeterminate. The sample is repeated once. If the repeat result is positive, the result will be reported as positive. If the result is negative or borderline, the result is reported as borderline. A follow-up sample will be requested 30 days after the initial sample.

(3) Positive; a distinct band is present at the 180 kD molecular weight relative to the positive controls. The sample is rerun at the dilutions of 1:3,000 and 1:10,000.

(n) Determination of Titer on Positive Sera Samples

Sample Dilution and Repeat Analysis

Samples are determined positive at the initial screen dilution of 1:300 are further diluted to determine final titer. Each positive sera was diluted 1:3,000 and 1:10,000. All other steps of the Western blot assay were performed as described above. Performance of sera diluted at 1:3,000 and 1:10,000 begins at Step 43 of the protocol. The sample strips were evaluated for botulinum specific bands as before. Sera was assigned a titer equivalent to the inverse of the highest dilution at which it is positive. A description designation of weakly, mildly, moderately or strongly positive is assigned according to titer (Table 1). Sera which are not positive a the higher dilutions are assigned a titer of 300.

(o) Reporting Results (1) Format

The confirmation of botulinum antibodies by the Western blot assay is dependent on the presence of a specific ban on the antigen blot. Positive serum will be identified by an antigen/antibody band at 180 kD (see FIG. 1). Positive results will be reported at the highest titer in which antibodies are detected (1:300, 1:3,000 or 1:10,000) along with the descriptive category for each sera (Table 1).

Sera with extremely weak or inconclusive band signal at the 180 kD molecular weight will be reported as borderline with a titer of <1.300. due to the indeterminate nature of this result, a second sample will be requested to follow the initial sample by 30 days.

Sera that do not display a band at the 180 kD weight are reported as negative.

TABLE 1

Result Categories and Titers

| "180 kD" Band | Dilution | Titer | Result | Category |
|---|---|---|---|---|
| Absent | 1:300 | 0 | Negative | Normal |
| Very Faint | 1:300 | <300 | Borderline | Weakly elevated |
| Present | 1:300 | 300 | Positive | Mildly elevated |
| Present | 1:3,000 | 3,000 | Positive | Moderately elevated |
| Present | 1:10,000 | >10,000 | Positive | Highly elevated |

(2) Limitations of the Assay

Antibody titers do not represent actual antibody concentration or activity at the target antigen. Titer values must be interpreted in context of the clinical presentation.

EXAMPLE

The blind study assays were performed using the exact Western blot protocol hereinabove described. Briefly, 22.5 mg of "crude" Botox antigen was electrophoresed on 10% acrylamide gels run in tris/glycine buffers. The antigen was electrotransferred to nitrocellulose, which was blocked and cut into individual strips. Each blot yielded 25 assay strips which allowed the analysis of 22 blind samples and 3 controls sera. Sera samples were diluted 1:300 in TBST buffer and incubated with the antigen strips for 2 hours at room temperature. Following three 10-minute washes, a second, goat anti-human, alkaline phosphatase labeled antibody was added to the strips. The second antibody was allowed to incubate for 1 hour at room temperature. A second set of three 10-minute washes was performed, followed by the addition of a color solution, BCIP in NBT. Hydrolyzed by the alkaline phosphatase, the BCIP produced a colored band on strips exposed to sera containing antibodies to botulinum toxin. Sera with a band observed in the same location as the positive control and corresponding to the 180 kD molecular weight marker were identified as positive.

Blind Sample Performance

Fifty samples were selected for the blind study. These sera represented the entire range of analytical response detected by the assay. The samples were blinded and assigned a coded number (1–50). Samples were performed in groups of 44. This number corresponds to the number of assay strips available from two blots. Twenty-five strips were cut from each blot, totaling 50. Forty-four were used to assay blind samples and 6, three from each blot, for the controls. Each of the sera was run in at least three separate assays. Samples which displayed weak, difficult-to-interpret results were further analyzed for confirmation.

Grading of Results

Results of the blind assay were visually evaluated for the presence or absence of the 180 kD band established as the positive criteria for antibodies to botulinum toxin. Samples were tested at the single dilution of 1:300 for the presence or absence of a positive signal. The assay is very sensitive. Because of the sensitivity, the positive samples showed a wide range of signal intensity. To simplify the variety of positive responses, the results were reported using only three categories as described in Table 2.

TABLE 2

| Result Category | Descriptive Requirements |
| --- | --- |
| Negative | No band(s) observed at the 180 kD range |
| Weakly Positive | Light banding observed at the 180 kD range |
| Positive | Definitive banding observed at the 180 kD range |

The most difficult category to assign results was "weakly positive". While some sera clearly show faint bands, others were at the extreme range of visual distinction. Because these samples are also the most susceptible to minor variation between assays, repeat testing of the sample often provides confirmatory information. Weak samples such as these only pose problems when comparing one set of results to another, as in a blind study. In practical applications, these weak or borderline cases are so assigned into this well-defined group. Due to the dynamic nature of antibody production in patients, borderline individuals would be retested in 30 to 60 days following the initial sample. In this period, borderline or weakly positive individuals actively producing antibodies would become positives. Patients with persistent weak or indeterminate results would remain categorized as borderline and of questionable significance.

Analysis of Blind Results

The following is a summary of decoded blind samples and the concordance to their expected result (true positive and true negative). Table 3 contains the results of both assays listed within each sera category.

Of the 10 sera from immunized individuals, the assay correctly identified all 10. In each case the sera displayed clearly positive signals in a consistent manner.

Excellent concordance was observed in the on-responder group. The evaluation of these samples was of particular importance for the confirmation of the increased western sensitivity and concordance with the mouse bioassay. Of the 13 non-responder sera identified as positive in the mouse bioassay and in the Western assay, 12 of 13 were detected positive in the blind assays. One sample was incorrectly identified as negative.

The third group, the responders, also displayed good concordance. Of this group, 8 negative sera and one positive were correctly identified. Minor differences were found in 2 additional negatives in which very weak bonds were observed. These samples were assigned to the weakly positive category. One additional sample described as borderline in earlier assays was determined as negative in the blind study.

The last group consisted of 15 untreated (normal) individuals in which the original analysis determined that 13 were negative, 1 was positive and 1 was borderline (indeterminate). The blinded assays correctly identified 11 of the negatives and the 1 positive. The borderline sample was identified as negative in the blind assays. In contract to the expected result, 1 normal was identified as positive and a second as weakly positive.

Conclusion

The results show the validity of the assay through the successful analysis of previously categorized sera at a concordance of greater than 90%. Of particular importance was the assay's ability to detect positive sera at a level equivalent to the mouse bioassay with the advantages of a Western blot assay.

Currently, the mouse bioassay is the standard assay for detection of antibodies to botulinum toxin in humans. Though the bioassay relies on indirect analysis of an $LD_{50}$ response, it does predict the presence of neutralizing antibodies. The major advantage of the Western blot assay is its ability to directly visualize the botulinum antibody/toxin complexes at a known molecular weight. In addition, the assay provides direct titers of patient sera. The strengths of the bioassay, which include its ability to only identify sera with neutralizing antibodies, have been incorporated into the Western.

TABLE 3

Blind Sample Data Sheet

|  | Sample Type | Result | Blind ID | Blind Result |
|---|---|---|---|---|
| 1 | Immunized | Pos | 25 | Pos |
| 2 | Immunized | Pos | 6 | Pos |
| 3 | Immunized | Pos | 42 | Pos |
| 4 | Immunized | Pos | 15 | Pos |
| 5 | Immunized | Pos | 4 | Pos |
| 6 | Immunized | Pos | 29 | Pos |
| 7 | Immunized | Pos | 10 | Pos |
| 8 | Immunized | Pos | 41 | Pos |
| 9 | Immunized | Pos | 14 | Pos |
| 10 | Immunized | Pos | 24 | Pos |
| 11 | Non-Responder | Pos | 33 | Pos |
| 12 | Non-Responder | Pos | 11 | Pos |
| 13 | Non-Responder | Pos | 39 | Pos |
| 14 | Non-Responder | Pos | 49 | Pos |
| 15 | Non-Responder | Bdr | 27 | W. Pos |
| 16 | Non-Responder | Pos | 28 | Pos |
| 17 | Non-Responder | Pos | 36 | Neg |
| 18 | Non-Responder | Pos | 18 | Pos |
| 19 | Non-Responder | Pos | 7 | Pos |
| 20 | Non-Responder | Pos | 48 | Pos |
| 21 | Non-Responder | Pos | 48 | W. Pos |
| 22 | Non-Responder | Pos | 50 | W. Pos |
| 23 | Non-Responder | Bdr | 22 | W. Pos |
| 24 | Responder | Neg | 9 | Neg |
| 25 | Responder | Neg | 21 | W. Pos |
| 26 | Responder | Neg | 38 | Neg |
| 27 | Responder | Neg | 8 | Neg |
| 28 | Responder | Neg | 16 | Neg |
| 29 | Responder | Neg | 47 | Neg |
| 30 | Responder | Neg | 40 | Neg |
| 31 | Responder | Neg | 20 | Neg |
| 32 | Responder | Neg | 26 | Neg |
| 33 | Responder | Pos | 30 | Pos |
| 34 | Responder | Bdr | 44 | Neg |
| 35 | Responder | Neg | 12 | W. Pos |
| 36 | Normal | Bdr | 19 | Neg |
| 37 | Normal | Neg | 13 | Neg |
| 38 | Normal | Neg | 35 | Neg |
| 39 | Normal | Neg | 23 | W. Pos |
| 40 | Normal | Neg | 43 | Neg |
| 41 | Normal | Neg | 3 | Neg |
| 42 | Normal | Neg | 34 | Neg |
| 43 | Normal | Neg | 32 | Neg |
| 44 | Normal | Neg | 17 | Pos |
| 45 | Normal | Pos | 31 | Pos |
| 46 | Normal | Neg | 37 | Neg |
| 47 | Normal | Neg | 2 | Neg |
| 48 | Normal | Neg | 5 | Neg |
| 49 | Normal | Neg | 1 | Neg |
| 50 | Normal | Neg | 45 | Neg |

Although there has been hereinabove described a botulinum toxin assay in accordance with the present invention, for the purpose of illustrating the manner in which the invention may be used to advantage, it should be appreciated that the invention is not limited thereto since many obvious modifications can be made, and it is intended to include within this invention any such modifications as will fall within the scope of the appended claims. Accordingly, any and all modifications, variations, or equivalent arrangements which may occur to those skilled in the art, should be considered to be within the scope of the present invention as defined in the appended claims.

What is claimed is:

1. An assay for detecting the presence of botulinum toxin neutralizing antibodies in a serum sample by visual identification of an antibody/antigen complex, said assay comprising:
    a) obtaining serum from a patient suspected of having developed neutralizing antibodies to botulinum toxin;
    b) separating a botulinum toxin protein complex which has not been treated with either sodium dodecyl sulfate or trypsin by acrylamide gel electrophoresis, said separation occurring based on protein size and charge;
    c) electrophoretically transferring separated toxin portions onto a solid support wherein each separated toxin protein is bound to the solid support at spaced apart sites;
    d) blocking all remaining binding sites on the solid support;
    e) contacting the solid support of step (d) with said patient serum sample;
    f) contacting the solid support of step (e) with an enzyme labeled anti-human Ig antibody;
    g) contacting the solid support of step (f) with a chromogenic substrate which reacts with said labeling enzyme to produce a colored precipitate; and
    h) correlating the presence of any colored precipitate formed at one or more sites on the solid support of step (g) which contains a separated toxin protein to the presence of said botulinum toxin neutralizing antibodies in said human serum sample.

2. The assay according to claim 1 wherein said solid support comprises nitrocellulose.

3. The assay according to claim 2 further comprising the step of drying the nitrocellulose after the electrophoretic transfer and before blocking in order to improve protein binding.

4. The assay according to claim 3 wherein said step of blocking all remaining sites comprises soaking the solid support in a blocking agent.

5. The assay according to claim 4 wherein said blocking agent comprises nonfat dried milk.

6. The assay according to claim 5 wherein said acrylamide gel comprises about 7.5% acrylamide.

7. The assay according to claim 6 wherein said labeling enzyme is alkaline phosphatase.

* * * * *